US00PP25004P2

(12) United States Plant Patent
Kordes

(10) Patent No.: US PP25,004 P2
(45) Date of Patent: Oct. 28, 2014

(54) MINIATURE ROSE PLANT NAMED 'KORPOT028'

(50) Latin Name: *Rosa hybrida*
Varietal Denomination: KORpot028

(71) Applicant: Tim-Hermann Kordes, Klein Offenseth-Sparrieshopp (DE)

(72) Inventor: Tim-Hermann Kordes, Klein Offenseth-Sparrieshopp (DE)

(73) Assignee: W. Kordes' Söhne Rosenschulen GmbH & Co KG, Offenseth-Sparrieshoop (DE)

( * ) Notice: Subject to any disclaimer, the term of this patent is extended or adjusted under 35 U.S.C. 154(b) by 0 days.

(21) Appl. No.: 13/986,586

(22) Filed: May 15, 2013

(51) Int. Cl.
*A01H 5/00* (2006.01)

(52) U.S. Cl.
USPC ..... Plt./122

(58) Field of Classification Search
USPC ..... Plt./122
See application file for complete search history.

*Primary Examiner* — Kent L Bell

(57) ABSTRACT

A new and distinct variety of rose with long lasting, novel dark red flowers, and attractive foliage with good disease resistance. It exhibits upright to bushy growth with abundant flowers. The new variety propagates well from cuttings and by grafting. This new and distinct variety has shown to be uniform and stable in the resulting generations from asexual propagation.

1 Drawing Sheet

Latin name of genus and species: The botanical classification of the new rose plant is *Rosa hybrida.*

Variety denomination: The denomination of the new variety is 'KORpot028'.

CROSS REFERENCES AND FEDERAL R&D STATEMENT

There are no cross referenced or related applications. This variety was developed without the aid of any research grant.

The new variety of rose plant of the present invention originated from a controlled crossing in a breeding program of two distinct parents during the summer of 2009. The crossing was between an 'un-named seedling', the seed parent, and another 'un-named seedling', the pollen parent by the same inventor.

The resulting seeds were planted during the following winter. The resulting seedlings were evaluated and exhibited distinctive physical and biological characteristics. The new rose plant was selected as a single plant from the seedling beds due to its superior characteristics and asexually propagated for further evaluation. This new and distinctive rose variety is named 'KORpot028'.

SUMMARY OF THE INVENTION

The new rose plant may be distinguished from its seed parent, an 'un-named seedling', by the following combination of characteristics:

1. 'KORpot028' has a very good shelf life, whereas the 'un-named seedling' had a good shelf life.
2. 'KORpot028' has a moderately large sized flower, whereas the 'un-named seedling' has a medium sized flower.

The new rose plant may be distinguished from its pollen parent, an 'un-named seedling', by the following combination of characteristics:

1. 'KORpot028' has a dark red flower, whereas the 'un-named seedling' has an orange-red flower.
2. 'KORpot028' has a double petal count, whereas the 'un-named seedling' has a very double petal count.

The objective of the hybridization was to create a new and distinct rose plant with unique qualities, such as:

1. Compact and uniform growth and flowering under greenhouse conditions when grown as a potted floral plant;
2. Abundant, long lasting, and attractive flowers and foliage;
3. Resistance to diseases encountered in greenhouse and nursery culture; and
4. Suitability for production from softwood cuttings in floral and nursery containers.

This combination of qualities is not present in prior rose cultivars known to the inventor. These objectives have been substantially achieved and in that distinguish 'KORpot028' from all other varieties of which I am aware.

As part of a rose development program, Tim-Hermann Kordes germinated seeds from the aforementioned hybridization and conducted evaluations and observations on the resulting seedlings in a controlled environment in Offenseth-Sparrieshoop, Germany. The resulting seedlings exhibited distinctive physical and biological characteristics. The new rose plant 'KORpot028' was selected in April 2010 from the seedling beds to be asexually propagated for further evaluation. The first asexual propagation of 'KORpot028' was done by rooting softwood cuttings in June 2010 at the inventor's nursery in Offenseth-Sparrieshoop, Germany.

These initial and other subsequent propagations conducted in controlled environments demonstrate that 'KORpot028' reproduces true to type in successive generations of asexual reproduction.

BRIEF DESCRIPTION OF THE DRAWING

The accompanying color drawing shows as true as is reasonably possible to obtain in color photographs of this type, the typical characteristics of the buds, sepals, reproductive organs, a flower, leaves, prickles, and stems of 'KORpot028'.

DETAILED BOTANICAL DESCRIPTION

The following is a description of 'KORpot028', as observed growing in April 2013 in a nursery in Jackson County, Oreg. on plants of 12 months of age. Color references are made using The Royal Horticultural Society (London, England) Colour Chart, 2001 except where common terms of color are used.

For a comparison, several physical characteristics of the rose variety 'KORpot003', a rose variety from the same inventor described and illustrated in U.S. Plant Pat. No. 23,795 and filed on Feb. 14, 2012 are compared to 'KORpot028' in Chart 1.

CHART 1

| Characteristic | 'KORpot028' | 'KORpot003' |
|---|---|---|
| Flower general tonality | Red Group 46A | Red Group 53A |
| Petal count | 30 | 55-65 |
| Bud form | Globular | Pointed ovoid |

Parents:

*Seed parent*.—An 'un-named seedling'.

*Pollen parent*.—An 'un-named seedling'.

Classification:

*Botanical classification*.—*Rosa hybrida* 'KORpot028'.

*Commercial classification*.—Miniature rose.

FLOWER AND FLOWER BUD

Blooming habit: Recurrent. Moderately floriferous.

Flower bud:

*Size*.—Upon opening, 20-32 mm in length from base of receptacle to distal end of bud and 18 mm diameter at its widest point.

*Bud form*.—Medium. Globular.

*Bud color*.—As sepals first unfold, bud color is Red Group 46A. When ¼ open, the upper surface of petals is Red Group 46A with intonations of Greyed-Purple Group 187B; and the lower surface is Red Group 46A. Lower surface of guard petals are Red Group 46A, with a limited number of guard petals with intonations of Green Group 143C. Limited number of guard petals have stripes of Green-White Group 157A, less frequently with Green Group 143C on lower surface.

*Sepals*.—Color: Upper surface Yellow-Green Group 146B. Lower surface Yellow-Green Group 146C. Distal ends of immature sepals show intonations of Greyed-Purple Group 183C. Size: Average 32-34 mm (l)×10-11mm (w). Shape: Weak foliaceous appendages on 3 of the five sepals. Apex: Mostly apiculate, some moderately cirrose. Base: Flat at union with receptacle. Quantity: Five. Surface texture: Upper side: Pubescent with numerous white hairs. Lower surface: Lightly pubescent with limited numbers of stipitate glands. Margins: Lightly pubescent with limited number of stipitate glands.

Flower bloom:

*Fragrance*.—Lightly fragrant.

*Duration*.—On the plant 18 to 24 days.

*Size*.—Moderately large for a miniature rose. When open, the average flower diameter is 60 mm and the average flower height is 35-40 mm.

*Form*.—Shape of flower when viewed from the side: Upon opening, upper part: Convex. Upon opening, lower part: Flattened convex. Open flower, upper part: Flat. Open flower, lower part: Flat.

Color:

*Upon opening, petals*.—Outermost petals: Outer Side: Red Group 46A. Inner Side: Red Group 46A.

*Innermost petals*.—Outer Side: Red Group 46A. Inner Side: Red Group 46A.

*Upon opening, basal petal spots*.—Basal petal spot, outermost petals: Outer Side: Green-Yellow Group 1C. Inner Side: Green-Yellow Group 1B. Basal petal spot, innermost petals: Outer Side: Green-Yellow Group 1B. Inner Side: Green-Yellow Group 1B.

*After opening, petals*.—Outermost petals: Outer Side: Red Group 46A. Inner Side: Red Group 46A with intonations of Greyed-Purple Group 187B. Innermost petals: Outer Side: Red Group 46A. Inner Side: Red Group 46A.

*After opening, basal petal spots*.—Basal petal spot, outermost petals: Outer Side: Yellow Group 2C. Inner Side: Yellow Group 2C. Basal petal spot, innermost petals: Outer Side: Green-Yellow Group 1C. Inner Side: Yellow Group 2B.

General tonality: On open flower Red Group 46A. No change in the general tonality at the end of the 15$^{th}$ day. Afterwards, general tonality is Red Group 46C.

Petals:

*Petal count*.—Double.

*Average range*.—Approximately 30 petals under normal conditions.

*Petal reflex*.—Limited.

*Petal margin*.—Mostly entire with some emargination.

*Petal shape*.—Deltoid to orbicular. Apex shape is rounded to obtuse. Shape of base is obtuse.

*Petal size*.—24-26 mm (l)×30-35 mm (w).

*Thickness*.—Average.

*Petal arrangement*.—Formal.

Petaloids:

*Petaloid count*.—Average of 6-8 per flower.

*Petaloid size*.—12-16 mm (l)×5-10 mm (w).

*Petaloid color*.—Color of inner side is Red Group 46A. Color of outer side is Red Group 46A. Intonations of Green-White Group 157A and Yellow Group 2C transitioning to Red Group 46A on inner and outer sides.

*Petaloid texture*.—Smooth and satiny.

*Margins*.—Variable, entire to erose.

*Petaloid shape*.—Variable, oblong to spatulate, with some petaloids highly irregular. Apex: Obtuse. Base: Obtuse.

Reproductive organs:

*Pistils*.—Abundant. Approximately 80+ present. Stigmas: Location: Slightly superior in position to anthers. Color: Greyed-Yellow Group 161D. Styles: Length: About 10-12 mm long. Color: Red-Purple Group 61B.

*Stamens*.—Approximately 100 on average and regularly arranged. Anthers: Size: Average 2-3 mm (l)×1½ mm (w). Pollen: Generally present. Color: Yellow-Orange Group 22A. Filaments: Color: Yellow Group 2A transitioning to Red Group 47B. Length: 3-4 mm.

*Receptacle*.—Surface: Nearly glabrous, with a few small white hairs. Color: Green Group 146C. Shape: Urn-shaped. Texture: Smooth. Size: 8-9 mm (h)×9-10 mm (w).

*Pedicel*.—Variable in size. Many pedicels with bracts. Surface: Moderate numbers of stipitate glands. Length: 40-45 mm average length. Diameter: 2-3 mm average diameter. Color: Green Group 146C. Strength: Strong. Texture: Smooth. Borne: Multiple flower buds per stem, generally 2 to 5. Flowers held upright.

*Peduncle*.—Length: 50-60 mm average length. Diameter: 4 mm average diameter. Color: Green Group 146C. Light intonations of Greyed- Purple Group 183C on juvenile peduncle. Strength: Strong. Texture: Smooth with limited number of stipitate glands and a few small prickles.

THE PLANT

*Growth*.—Moderately vigorous.

*Plant habit*.—Upright to bushy habit. When grown as a 10.5 cm pot plant, the average plant height is 25 cm and the average plant width is 15 cm.

*Stems*.—Stem color: Young wood: Green Group 146C. Older wood: Green Group 146B. Stem surface: Young wood: Smooth. Older wood: Smooth.

*Prickles*.—Present. Incidence: Variable. 15-25 per 10 cm on many stems. Often with numerous smaller prickles. Size: Variable. 1-6 mm long on average. Color: Immature prickles: Greyed-Orange Group N170C. Mature prickles: Greyed-Orange Group N170D. Senescing to Greyed-Orange Group 164D. Shape: Concave. Anthocyanin color: Greyed-Orange Group N170B.

*Leaves*.—Normally 5-7 leaflets on normal leaves in middle of the stem. Venation pattern: Pyramidal net pattern. Leaf size: 120-135 mm (l)×75-80 mm (w). Abundance: Very abundant.

*Leaflets*.—Size: Average size of the terminal leaflet is 60 mm (l)×30 mm (w). Shape: Ovate. Base: Obtuse. Apex: Acute. Margins: Finely serrated. Surface: Upper: Semi-glossy, smooth. Lower: Matte, rough. Texture: Somewhat coriaceous. Arrangement: Odd pinnate. Venation Reticulate. Color, mature foliage: Upper Leaflet Surface: Green Group 137A. Lower Leaflet Surface: Greyed-Green Group 191A. Color, juvenile foliage: Upper Leaflet Surface: Green Group 137A. Lower Leaflet Surface: Green Group 138B. Anthocyanin intonation: Intonations of Greyed-Purple Group 187A present on juvenile leaflet, petiole, rachis and stipule.

*Stipules*.—Size: 18-20 mm (l)×6-8 mm (w). Stipule color: Green Group 146C. Anthocyanin: Greyed-Purple Group 183C. Stipitate glands: Abundant. Margins: Entire to erose. Shape: Apex: Apiculate. Base: Flat.

*Petiole*.—Length: Average 10-30 mm. Diameter: Average 2 mm. Petiole color: Green Group 146A. Underneath: Green Group 146B. Margins: With small white hairs and limited numbers of stipitate glands. Anthocyanin: Greyed-Purple Group 183C. Prickles: Generally 1-2 underneath. Stipitate Glands: Limited. Texture: Smooth.

*Petiole rachis*.—Length: Average 10-30 mm. Diameter: Average 2 mm. Color: Green Group 146A. Anthocyanin present on juvenile tissue. Greyed-Purple Group 183C. Margins: With small white hairs and limited numbers of stipitate glands. Prickles: A few small prickles underneath. Stipitate glands: Limited numbers of stipitate glands on margins. Texture: Smooth.

Hips/seed formation: None observed.

Winter hardiness: Unknown.

Disease resistance: Good resistance to Powdery mildew (*Sphaerotheca pannosa*) and Botrytis (*Botrytis cinerea*) diseases under normal greenhouse growing conditions in Jackson County, Oreg.

I claim:

1. A new and distinct variety of rose plant, as described and illustrated herein.

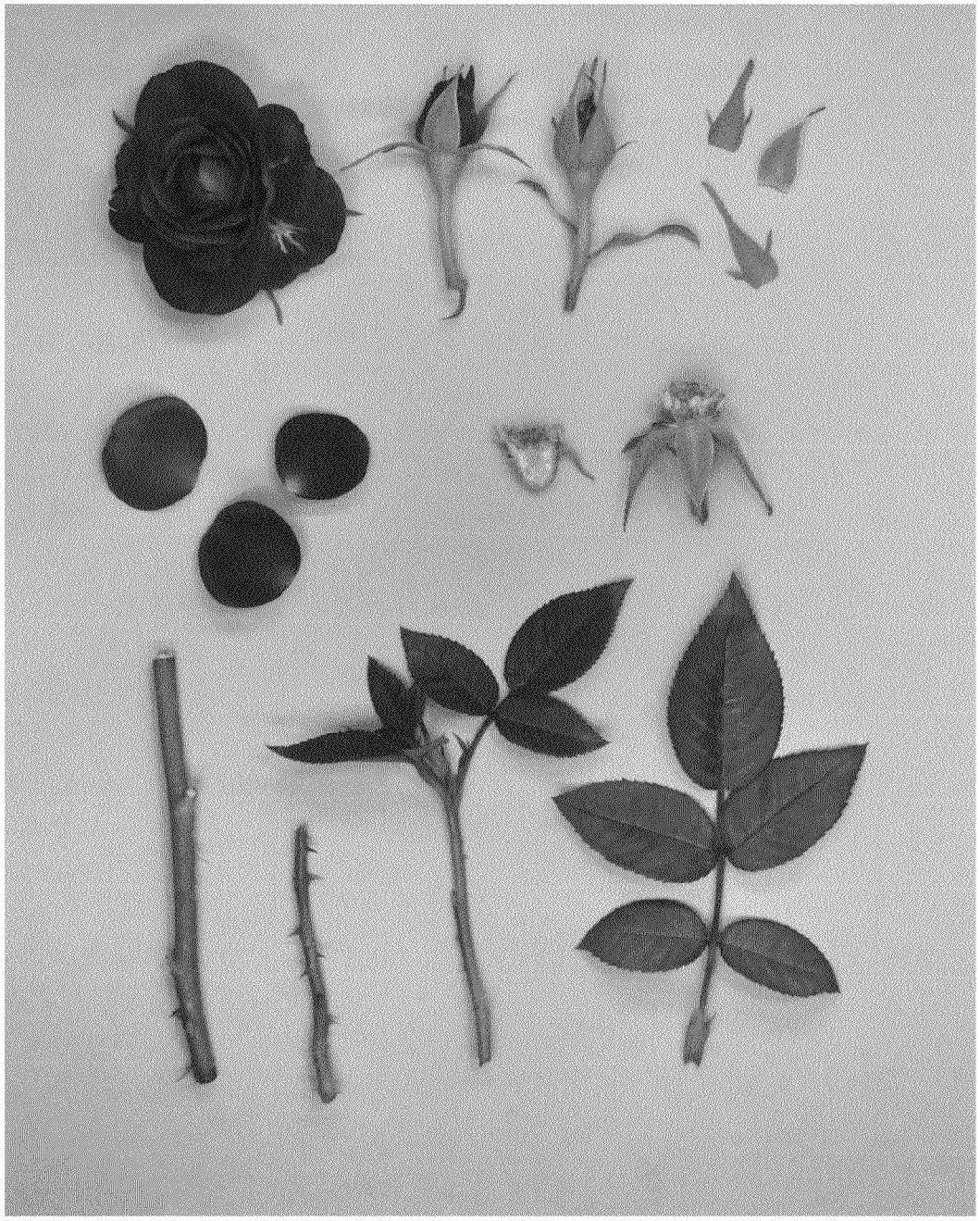

* * * * *